United States Patent
Frierson

(10) Patent No.: US 8,864,696 B1
(45) Date of Patent: *Oct. 21, 2014

(54) TOE CURL PREVENTION DEVICE AND METHODS

(71) Applicant: Deborah Frierson, Hermitage, TN (US)

(72) Inventor: Deborah Frierson, Hermitage, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/746,946

(22) Filed: Jan. 22, 2013

Related U.S. Application Data

(63) Continuation of application No. 12/947,918, filed on Nov. 17, 2010, now Pat. No. 8,357,110.

(51) Int. Cl.
*A61F 5/00* (2006.01)

(52) U.S. Cl.
USPC .................................. 602/23; 602/28; 602/30

(58) Field of Classification Search
USPC .................. 602/23–30; 2/239, 240; 128/882; 482/907
See application file for complete search history.

(56) References Cited

U.S. PATENT DOCUMENTS

| | | | | |
|---|---|---|---|---|
| 3,527,209 A * | 9/1970 | Baker | ............................ | 602/28 |
| 4,566,447 A * | 1/1986 | Deis | ................................ | 602/28 |
| 5,399,155 A * | 3/1995 | Strassburg et al. | ............ | 602/28 |
| 6,790,165 B2 * | 9/2004 | Huang | ............................ | 482/79 |
| 7,611,477 B2 * | 11/2009 | Dayhoff et al. | ................. | 602/29 |
| 7,806,844 B2 * | 10/2010 | Outred et al. | ................... | 602/28 |

\* cited by examiner

*Primary Examiner* — Michael A. Brown
(74) *Attorney, Agent, or Firm* — Waddey Patterson PC; Matthew C. Cox

(57) ABSTRACT

An apparatus and associated methods for preventing and treating toe curl, a condition where the toes of a patient curl toward the bottom of the foot, are provided. The apparatus provides a pad operable for engaging the bottom of the foot, and a strap that surrounds the foot and pad for applying a flexion force against the foot. The pad engages and supports at least one toe and prevents the toe or toes from curling toward the bottom of the foot. The device can be worn by a patient at night or during the day to treat or prevent toe curl. Additionally, the strap can include an elastic material for providing a tension force required for flexion stretching, and the strap can be attachable at one end to a removable leg band that can be securely and releasably positioned about the leg.

14 Claims, 3 Drawing Sheets

TOE CURL PREVENTION DEVICE AND METHODS

CROSS-REFERENCES TO RELATED APPLICATIONS

This application is a continuation of co-pending U.S. patent application Ser. No. 12/947,918 filed Nov. 17, 2010 entitled "TOE CURL PREVENTION DEVICE AND METHODS" all of which is hereby incorporated by reference in its entirety.

BACKGROUND

1. Technical Field

The present invention relates to devices and methods for preventing and treating foot disorders. More particularly, the present invention relates to foot support devices and methods for preventing and treating toe-curl associated with spinal cord injury and other medical conditions.

2. Background Art

Patients suffering from various types of spinal cord injuries and other medical conditions can experience a phenomenon where the toes uncontrollably curl toward the bottom of the foot, forming a curled or claw-like shape. The curling can be due to spasticity in the muscles and tendons in the foot or can be caused by tightening of the tendons and muscles in the foot due to long periods of non-use. Over time, the movement of the foot tendons and muscles can permanently deform and disfigure the toes, result in a claw-toe, or hammer-toe. Toe curl deformation of this type is particularly prevalent among spinal cord injury patients, patients with multiple sclerosis, and stroke victims. The toe curl deformation process can occur over several months or years, and can cause a variety of associated medical problems which may require additional medication or surgery, including poor circulation, pain and infection. Additionally, the condition can prevent a patient from being able to wear shoes or slippers. Toe curl deformation also causes patients to experience mental anguish due to the deformed visual appearance of the toes.

Others have attempted to address the problems associated with toe curl by providing surgical techniques and tools to cut open and relieve the tension on the ligaments in the foot that contribute to the problem. Still others have developed injectable pharmaceuticals that can be locally administered to relax the tightened ligaments and prevent the condition. However, such conventional treatments do not address the problem before it begins and can be very expensive.

What is needed then is a device and associated methods for preventing and treating toe curl deformation in human feet.

BRIEF SUMMARY

One aspect of the present invention provides an apparatus for preventing toe curl by supporting a foot and corresponding toes, each toe having a distal toe end extending away from the foot. The apparatus includes a pad engaging the bottom of the foot and extending to the distal toe end of at least one toe when the pad is positioned on the foot. The apparatus also includes a leg band and a strap having a proximal strap end attached to the leg band. The strap includes a distal strap end securable to the pad, and the strap includes a resilient material. The strap spans the distance between the leg band and the pad when the strap distal end is secured to the foot.

Yet another aspect of the present invention provides an apparatus for preventing the toes of a foot from curling toward the bottom of the foot. The apparatus includes a pad operable to engage the foot, the pad contacting the underside of at least one toe when the pad is positioned on the foot. The apparatus also includes a foot sleeve defining a sleeve opening shaped for receiving the foot and the pad, wherein the foot sleeve is operable to at least partially surround the foot and the pad when the pad is positioned adjacent the foot. The apparatus further includes a leg band and a strap having a proximal strap end attached to the leg band. The strap includes a distal strap end extending away from the leg band and defining a strap opening. A heel cushion is positioned adjacent the bottom of the foot. The heel cushion defines a central depression shaped for receiving the foot in some embodiments.

A further aspect of the present invention provides a method of preventing toe curl in a foot of a spinal cord injury patient. The method includes the steps of: (a) providing a foot support device having a pad, a foot sleeve, a leg band, an elastic strap attached to and extending from the leg band, the strap defining a strap hole shaped for receiving the foot, and a heel cushion; (b) positioning the pad adjacent the bottom of the foot so that the pad contacts the underside of at least one toe; (c) positioning the foot sleeve over both the pad and the foot; (d) positioning the leg band on the leg between the patient's foot and hip; (e) stretching the elastic band toward the foot; and (f) inserting the foot, pad and foot sleeve through the strap hole, thereby securing the strap to the foot in a stretched position and applying a flexion force on the foot directed toward the knee.

Numerous other objects, features and advantages of the present invention will be readily apparent to those skilled in the art upon a reading of the following disclosure when taken in conjunction with the accompanying drawings.

DETAILED DESCRIPTION

Figure 6:
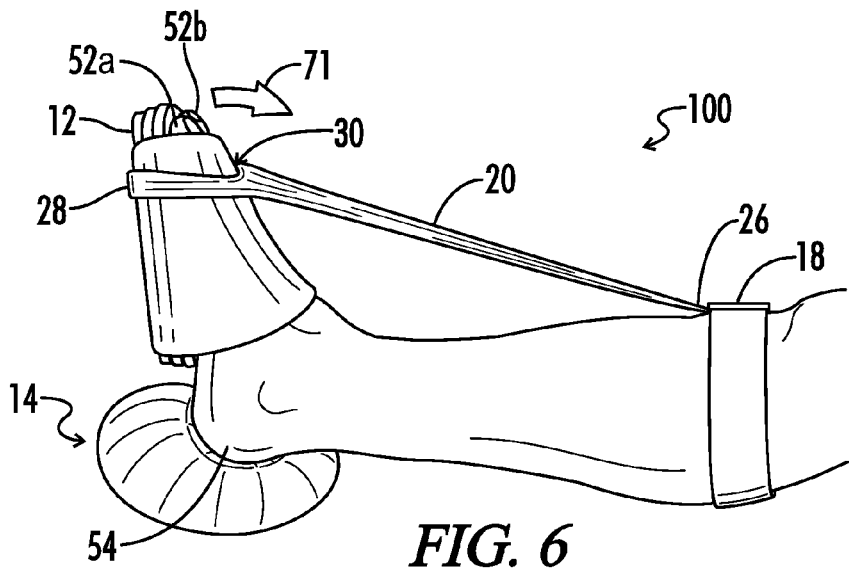
FIG. 6 illustrates a partial perspective view of an embodiment of a leg support apparatus in accordance with the present invention showing the strap opening positioned over the foot.

Referring now to the drawings, FIG. 6 illustrates a perspective view of an embodiment of a toe curl prevention apparatus generally designated by the numeral 100. In the drawings, not all reference numbers are included in each drawing for the sake of clarity. In addition, positional terms such as "upper," "lower," "side," "top," "bottom," etc. refer to the apparatus when in the orientation shown in the drawing. The skilled artisan will recognize that the apparatus can assume different orientations when in use.

Figure 1:
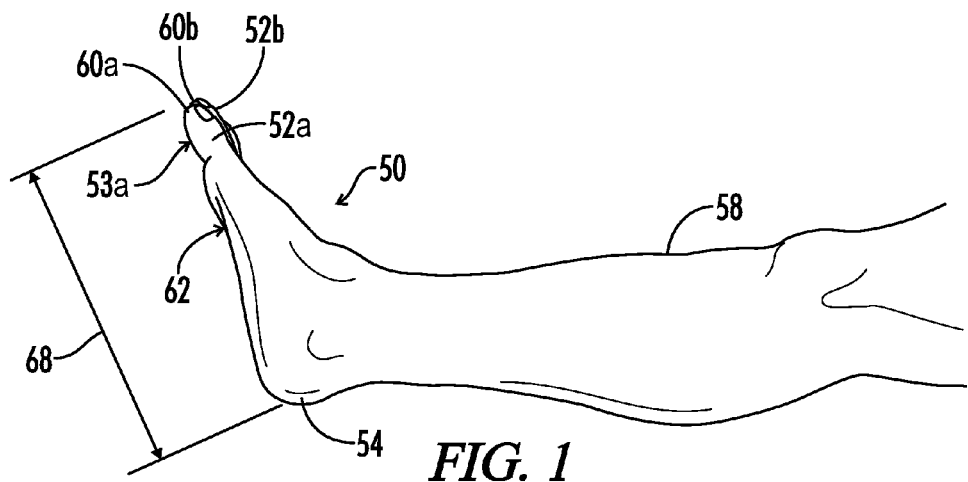
FIG. 1 illustrates a side perspective view of an embodiment of a leg and a foot.

Referring now to FIG. 1 a human foot 50 is generally illustrated. The foot includes a plurality of toes 52*a*, 52*b*, etc. Each toe has a distal toe end 60*a*, 60*b*, etc., respectively. Each distal toe end extends away from the foot 50. Each toe 52*a*, 52*b*, etc. also includes a toe underside 53*a*, etc. Each toe underside generally faces away from the leg 58. The foot 50 also includes an arch 62 defined along the bottom of the foot. The arch 62 separates the toes from the heel 54. A toe joint is positioned between the toe 53*a* and the arch 62. The foot 50 includes a foot length 68 extending from the heel 54 to the distal toe ends 60*a*, 60*b*, etc. The foot length 68 is generally defined as the length from the heel 54 to the most distal toe end, usually first distal toe end 60*a* or second distal toe end 60*b*.

Figure 2:
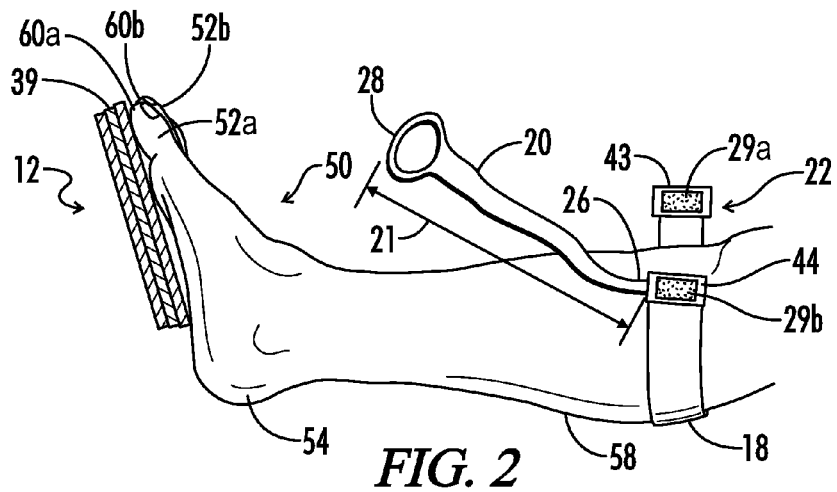
FIG. 2 illustrates a partial side perspective view of an embodiment of a foot support apparatus in accordance with the present invention.

As seen in FIG. 2, an embodiment of the present invention provides a pad 12, or foot pad, that can be positioned along the underside of the foot 50 adjacent the arch 62. The foot pad 12 in some embodiments engages the bottom of the foot and extends to the toe distal end 60*a*, 60*b*, etc. of at least one toe 52*a*, 52*b*, etc. when positioned on the foot 50. A leg band 18 is positioned on the leg 58 between the foot 50 and the patient's hip (not shown). A strap 20 has a proximal strap end 26. The proximal strap end 26 is attached to the leg band 18. Strap 20 also has a distal strap end 28 extending away from the leg band 18. The distal strap end 28 is securable to the foot pad 12 by a mechanical attachment means or by a press fit or tension fit.

Strap 20 includes a resilient material or stretchable fabric in some embodiments. Strap 20 can include an elastomer such as natural rubber, synthetic rubber, butyl rubber, latex, nitrile rubber, silicone rubber, combinations thereof or other suitable resilient or stretchable materials. Strap 20 can include an unstretched length 21, seen in FIG. 2. In some embodiments, the unstretched length 21 is between about two and about twenty inches, depending on the length of the patient's leg.

Figure 5A:
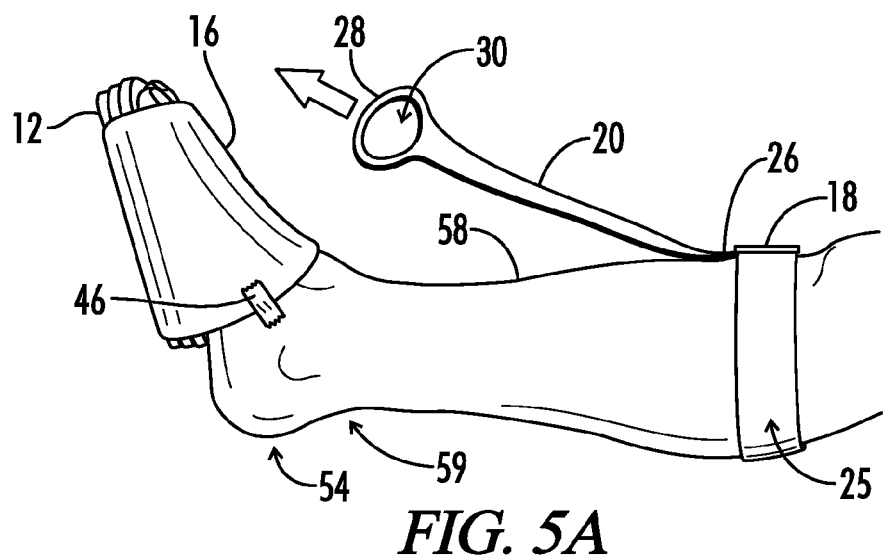
FIG. 5A illustrates a partial side perspective view of an embodiment of a foot support apparatus positioned on the leg of FIG. 1.
Figure 5B:
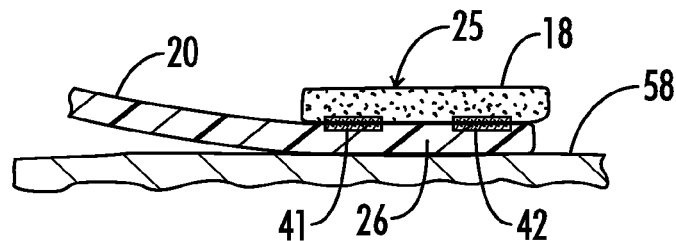
FIG. 5B illustrates a partial detail cross-sectional view of an embodiment of a strap and leg band.

Referring further to FIG. 2, in some embodiments, both strap 20 and leg band 18 include a fabric material. Strap 20 can be sewn directly to leg band 18 in some embodiments, as seen in FIG. 5B. For example, leg band 18 can include an annular band positioned around the circumference of leg 58, and strap proximal end 26 of strap 20 can be positioned between leg band 18 and leg 58. Strap proximal end 26 can also be sewn directly to leg band 18 at a first stitch region 41. First stitch region 41 can include a sewn connection between leg band 18 and strap 20. Similarly, in some embodiments, a second stitch region 42 can be used to secure strap 20 to leg band 18. In other embodiments, leg band 18 can be attached to strap 20 using mechanical fasteners such one or more buttons, snaps, hook-and-loop fasteners or other suitable fasteners. Strap proximal end 26 is generally positioned on the side of leg band 18 opposite the leg band outer surface 25 in some embodiments. However, in other embodiments not shown, strap proximal end 26 can be directly attached to leg band outer surface 25.

Referring further to FIG. 2, leg band 18 can include a releasable connection, or leg band closure 22, so that leg band 18 can be positioned on leg 58 without sliding leg band 18 over foot 50. A leg band closure 22 on leg band 18 also allows the leg band 18 to be positioned on the patient without requiring lifting heel 54. As seen in an exemplary embodiment in FIG. 2, leg band closure 22 includes a first band end 43 and a second band end 44. A first band fastener 29*a* is positioned on first band end 43, and a second band fastener 29*b* is positioned on second band end 44. First and second band fasteners 29*a*, 29*b* can include any suitable fasteners, including hook-and-loop fasteners, buttons, snaps, and the like. First band fastener 29*a* can generally be releasably secured to second band fastener 29*b*. Proximal strap end 26 can be attached to either first band end 43 or second band end 44.

Figure 3:
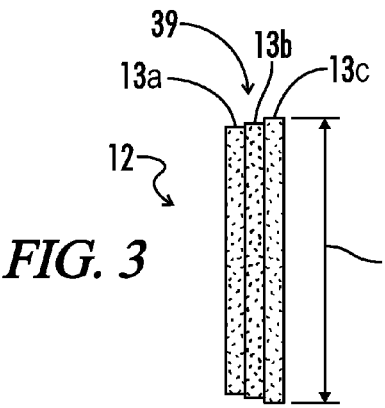
FIG. 3 illustrates a partial cross-sectional view the foot pad of FIG. 2.

Referring now to FIG. 3, in some embodiments, foot pad 12 includes a plurality of adjacent layers 13*a*, 13*b*, 13*c*, etc. Although foot pad 12 is illustrated in one embodiment in FIG. 3 as having three layers, in other embodiments foot pad 12 can have only one layer. In other embodiments, foot pad 12 can have between two and about ten layers. In yet further embodiments, foot pad 12 can have greater than ten layers. In some preferred embodiments, foot pad 12 includes five or six layers. Some or all layers in foot pad 12 can include a rigid material. Other layers can be flexible. In some embodiments, a first layer 13*a* includes a first material having a first density, and a second layer 13*b* includes a second material having a second density, wherein the first and second densities are not equal. Additionally, third layer 13*c* could have a third density different from the first and second densities. For example, the layer positioned nearest the foot might have a lower density than another layer to enhance comfort against the bottom of the foot. In yet other embodiments, it may be more desirable to include a more rigid, or denser, layer adjacent the bottom of the foot to enhance support. In some embodiments, one or more layers can include a foam or cushion material such as plastazote, Poron® cushioning foam, a polyethylene foam, a natural or synthetic leather material, a polyolefin such as but not limited to polypropylene, a graphite, a plastic, combinations thereof, or other suitable materials. It is understood that each layer 13*a*, 13*b*, 13*c*, etc. in foot pad 12 can include a similar or dissimilar material as compared to other layers in foot pad 12. For example, each layer might include a polyethylene foam. In other embodiments, first layer 13*a* and third layer 13*c* can include a polyethylene foam, and second layer 13*b* can include a more rigid material such as a graphite or a plastic. Additionally, one or more layers can include a gel-filled layer to improve comfort or to provide a desired heating or cooling effect to the foot during use.

Figure 8A:
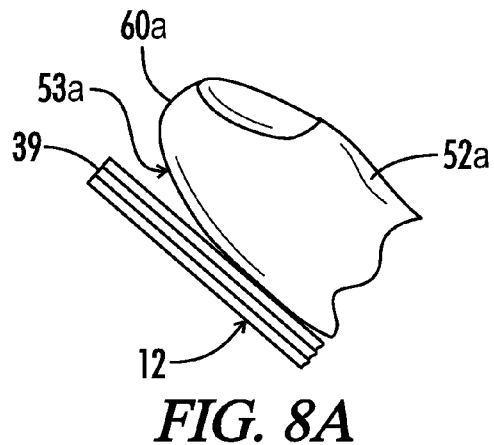
FIG. 8A illustrates a detail side view of an embodiment of a foot pad supporting a toe wherein the foot pad distal end extends to the toe distal end.
Figure 8B:
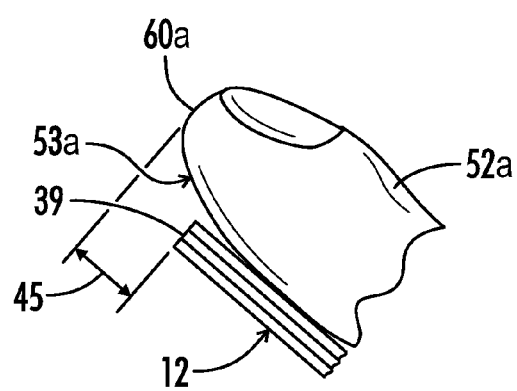
FIG. 8B illustrates a detail side view of an embodiment of a foot pad supporting a toe wherein the foot pad distal end does not extend completely to the toe distal end.

Referring further to FIG. 3, in some embodiments, foot pad 12 includes a foot pad length 37. As seen in FIG. 2, in some embodiments, foot pad 12 is generally positioned on foot 50 such that foot pad distal end 39 extends away from heel 54. In some embodiments, foot pad 12 is positioned adjacent foot 50 so that foot pad distal end 39 is aligned with at least one toe distal end 60*a*, 60*b*, etc. In some embodiments, foot pad 12 is positioned against foot 50 so that foot pad 12 extends to the distal end of at least one toe when foot pad 12 is positioned on the foot. For example, as seen in FIG. 8A, in some embodiments, foot pad 12 supports the underside 53*a* of first toe 52*a*. As seen in FIG. 8A, in some embodiments, distal toe end 60*a* can be aligned with foot pad distal end 39 when foot pad 12 is positioned on foot 50. In some other embodiments, foot pad distal end 39 can extend beyond one or more distal toe ends 60*a*, 60*b*, etc., as seen in FIG. 6. As seen in FIG. 8B, in some embodiments a foot pad 12 can be positioned against foot 50 so that foot pad distal end 39 supports the underside of the toe without extending completely to the toe distal end 60*a*. In such embodiments, the foot pad distal end 39 defines a pad offset distance 45 less than the total length of the toe, but greater than zero. In some embodiments, the ratio of pad offset distance 45 to toe length is between about 0.1 and about 0.9. In other embodiments, the ratio of pad offset distance 45 to toe length is about 0.5. It is understood that the toe described herein and represented in FIG. 8A and FIG. 8B can be any toe, and not necessarily the largest or longest toe.

Figure 4:
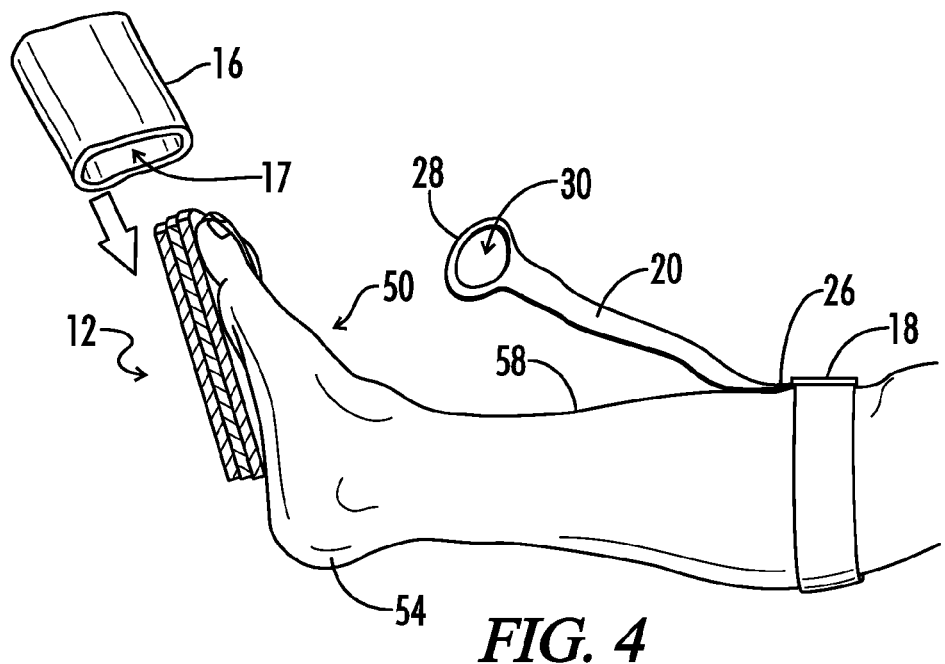
FIG. 4 illustrates a partially exploded side perspective view of an embodiment of a foot support apparatus in accordance with the present invention.

Referring now to FIG. 4, in some embodiments, strap 20 includes a distal strap end 28 that defines a strap opening 30. Strap opening 30 can be dimensioned to fit over the foot from the distal toe end toward the heel. The strap opening 30 can also include a stretchable or resilient material such as an elastomer so that strap opening 30 can initially have a smaller inner diameter than the outer diameter of the foot, but can stretch to conform to the shape of the foot when positioned onto the foot.

Also seen in FIG. 4, in some embodiments a foot sleeve 16 is provided to be positioned over the foot 50 and foot pad 12. The foot sleeve 16 includes a foot sleeve opening 17 shaped to receive the foot 50. The foot sleeve 16 is operable to at least partially surround foot 50 and pad 12 when positioned on the foot 50, as seen in FIG. 5A. The strap opening 30 is shaped for receiving the foot 50, foot sleeve 16 and foot pad 12, as seen in FIG. 6. Foot sleeve 16 can include a fabric material. In some embodiments, foot sleeve 16 includes a stretchable or resilient material such as an elastomer material.

When strap 20 is positioned on foot 50, as seen in FIG. 6, strap distal end 28 can be positioned along foot length 68 at various positions to achieve different levels of force. For example, a greater applied flexion force can be experienced when strap distal end 28 is positioned nearer a toe distal end 60a, 60b, etc. However, in other embodiments, a lower flexion force can be achieved by positioning strap distal end 28 nearer heel 54. In some embodiments, an optimal level of flexion force can be achieved for preventing toe curl when strap distal end 28 is positioned between the midpoint of foot length 60 and a toe distal end.

During use, the foot pad 12 is positioned against the foot 50. The foot sleeve 16 can be positioned over the foot to surround the foot 50 and the foot pad 12. In some embodiments, one or more pieces of adhesive tape 46 can be applied to the foot sleeve 16 to releasably secure the foot sleeve 16 to the foot 50. In some applications, because of the tapered shape of foot 50, the foot sleeve 16 may have a tendency to slip off the distal end of foot 50. Tape 46 can prevent such movement of foot sleeve 16. Tape 46 can include a surgical tape, a fabric athletic tape, or a household tape such as masking tape or duct tape. Leg band 18 is also positioned onto leg 58. Leg band 18 can be secured to leg 58 in some embodiment using leg band closure 22, seen in FIG. 2. Distal strap end 28 can be stretched, or pulled, toward foot 50, and strap opening 30 is positioned over foot 50, foot pad 12 and foot sleeve 16.

As seen in FIG. 6, when strap 20 is stretched and secured to pad 12, strap 20 includes a stretched length 23 such that strap 20 spans the distance between the leg band 18 and the pad 12. In this position, strap 20 exerts a flexion force on foot 50, as indicated by flexion arrow 71. The flexion force is transferred through foot pad 12 to toes 52a, 52b, etc., thereby supporting the underside of the toes. The support provided to the underside of the toes by pad 12 due to the flexion force supplied by strap 20 prevents toe curl. As seen in FIG. 6, in some embodiments an optimal flexion force is applied to the foot by positioning the distal strap end 28 at a location on the foot substantially between the a toe and the underside of the foot, or the arch 62. By positioning the distal strap end at a joint location where the toe meets the body of the foot between toe 53a and arch 62 seen in FIG. 1 and FIG. 6, a proper flexion force for preventing toe curl and foot droop can be achieved. It is understood that a proper flexion force can also be achieved by positioning distal strap end 28 at other locations along the foot 50.

The apparatus 100 seen in FIG. 6 can be worn by a user or a patient during times of reduced activity, such as at night during sleeping or when resting on a couch or bed. Repeated use in such instances will generally prevent the claw-tow, or hammer-toe, conditions commonly experienced by spinal cord injury patients, multiple sclerosis patients and stroke victims.

Figure 7:
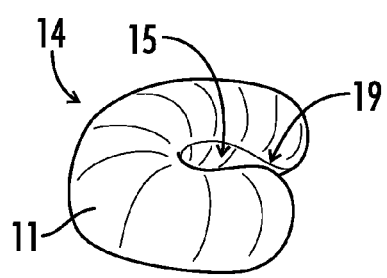
FIG. 7 illustrates an embodiment of a heel cushion in accordance with the present invention.

Referring now to FIG. 6 and FIG. 7, in some optional embodiments a heel cushion 14 can be positioned under heel 54 adjacent foot pad 12 during use of the apparatus 100. The heel cushion 54 in some embodiments includes a tubular cushion sleeve 11 filled with a cushioning material such as cushioning beads or pellets. In other embodiments, tubular cushion sleeve 11 can be filled with a soft material such as cotton a suitable padded stuffing material. In one embodiment, heel cushion 14 includes a tubular cushion sleeve 11 having an elastic nylon sleeve of the type used in nylon leg wear and filled with foam beads. The tubular cushion sleeve 11 in some embodiments can include first and second tube ends that can be tied together to form a toroidal, or doughnut-shaped, ring structure, as seen in FIG. 7. The heel cushion 14 in this embodiment defines a central depression 15 shaped to receive heel 54. A radial groove, or radial depression 19 can also be positioned near the junction of the first and second tube ends shaped to receive the Achilles region 59 of the leg adjacent the heel 54, seen in FIG. 5A. Heel cushion 54 can be used to prevent the formation of bed sores or breaks in the skin that commonly form on the heels of bedridden patients or patients with spinal cord injuries affecting the lower regions of the body. In addition, heel cushion 54 can be placed under one or both of the patient's feet to relieve pressure on a foot when turning the patient over on a side.

In addition, the foot support device of the present invention can be used to address a separate problem experienced by spinal cord injury patients and other types of patients wherein the one or both feet tend to droop or extend away from the leg, resulting in an unnatural extended foot position. This drooping effect can be caused by atrophy or non-use of the tendons in the leg. The drooping effect can also be caused by unbalanced tension forces in the tendons and muscles of the legs. The flexion force provided by the foot support apparatus 100 of the present invention, as illustrated as arrow 71 in FIG. 6, can prevent and treat the drooping effect.

In some embodiments, the present invention includes a method of preventing toe curl in a foot of a spinal cord injury patient. The method includes the steps of: (a) providing a foot support device having a pad, a foot sleeve, a leg band, an elastic strap attached to and extending from the leg band, the strap defining a strap hole shaped for receiving the foot, and a heel cushion; (b) positioning the pad adjacent the bottom of the foot so that the pad contacts the underside of at least one toe; (c) positioning the foot sleeve over both the pad and the foot; (d) positioning the leg band on the leg between the patient's foot and hip; (e) stretching the elastic band toward the foot; and (f) inserting the foot, pad and foot sleeve through the strap hole, thereby securing the strap to the foot in a stretched position and applying a flexion force on the foot directed toward the knee.

In additional embodiments, the method can include the step of providing a patient having a spinal cord injury. In another embodiment, the method can include the step of providing a patient having multiple sclerosis. In yet another embodiment, the method can include the step of providing a patient who is a stroke victim. Additionally, the method can include the step of positioning a heel cushion under the heel of the foot. Although the method can be described as a method of preventing toe curl, in some embodiments, the present invention includes a method of treating toe curl after it has already begun. In the treatment method, the various steps listed above may be present in some embodiments, and the objective of the treatment method is to prevent toe curl from worsening and to reverse the effects of toe curl. Additionally, using the treatment method described herein, the effects of toe curl may be diminished.

Thus, although there have been described particular embodiments of the present invention of a new and useful TOE CURL PREVENTION DEVICE AND METHODS, it is not intended for such references to be construed as limitations upon the scope of the invention except as set forth in the following claims.

What is claimed is:

1. An apparatus for preventing the toes of a foot from curling toward the bottom of the foot, comprising:
    a pad operable to support the underside of at least one toe when the pad is positioned against the foot;
    a leg band; and
    a strap having a proximal end attachable to the leg band and a distal strap end forming a strap opening,
    wherein the strap opening is shaped to receive a portion of the foot.

2. The apparatus of claim 1, further comprising a heel cushion defining a central depression shaped for receiving a portion of the foot.

3. The apparatus of claim 1, further comprising the pad including a plurality of adjacent layers.

4. The apparatus of claim 1, wherein the strap includes an elastomer material.

5. The apparatus of claim 1, wherein the strap is sewn to the leg band.

6. The apparatus of claim 1, wherein the leg band includes a releasable closure.

7. The apparatus of claim 1, further comprising a foot sleeve having a foot sleeve opening shaped for receiving the foot.

8. The apparatus of claim 1, wherein the pad extends to a distal end of at least one toe when the apparatus is positioned on the foot.

9. A method of preventing toe curl in a patient's foot, comprising:
    (a) providing a foot support device having a pad, a leg band, and a strap attachable to and extending from the leg band, the strap including a strap hole shaped for receiving a portion of the foot;
    (b) positioning the pad against the bottom of the foot so that the pad supports the underside of at least one toe;
    (c) positioning the leg band on the patient's leg;
    (d) pulling the leg band toward the foot; and
    (e) positioning a portion of the foot and the pad in the strap hole.

10. The method of claim 9, further comprising wherein the pad extends at least to the distal end of the at least one toe.

11. The method of claim 9, further comprising:
    positioning a heel cushion under the heel of the foot.

12. The method of claim 11, wherein the strap hole receives the foot and the pad.

13. The method of claim 9, further comprising:
    positioning a sleeve around the foot and the pad.

14. The method of claim 13, wherein the strap hole receives the sleeve.

* * * * *